US00PP09969P

United States Patent [19]

Cole

[11] Patent Number: Plant 9,969

[45] Date of Patent: Jul. 15, 1997

[54] IMPATIENS PLANT NAMED 'ORANGE ICE'

[75] Inventor: Douglas S. Cole, Loudon, N.H.

[73] Assignee: D.S. Cole Growers, Inc., Loudon, N.H.

[21] Appl. No.: 602,565

[22] Filed: Feb. 20, 1996

[51] Int. Cl.[6] ..... A01H 5/00

[52] U.S. Cl. ..... Plt./87.6

[58] Field of Search ..... Plt./87.6

*Primary Examiner*—James R. Feyrer

*Attorney, Agent, or Firm*—Foley & Lardner

[57] ABSTRACT

A new cultivar of *Impatiens sultani* plant named Orange Ice, characterized by its orange flower color, its fully double consistent flowers, and its variegated foliage consisting of a greyed-green main color, irregular patterns of lighter greyed-green mainly along and extending from the midrib, and white edges which extends variably from the margin toward the leaf midrib.

1 Drawing Sheet

The present invention comprises a new and distinctive cultivar of Impatiens plant, botanically known as *Impatiens sultani,* and know by the cultivar name Orange Ice. The species name appears to be synonymous with the species designation *I. walleriana,* also referred to in botanical literature.

The new cultivar is a sport or mutation of the unpatented cultivar Rosebud Orange, and was discovered by the inventor Douglas S. Cole in February 1994 in greenhouses in Concord, N.H. The mutation was discovered while taking cuttings of the parent cultivar, when one branch of one plant of the parent cultivar Rosebud Orange displayed variegated foliage, as opposed to the solid green foliage of the parent cultivar. The branch cutting was removed, planted, and grown out, with the variegation and foliage being commonly displayed throughout the plant. Subsequent asexual reproduction by terminal or stem cuttings taken by the inventor in Concord, N.H. has shown that the unique features of this new cultivar are stabilized and are reproduced true to type in successive propagation.

The following characteristics taken in combination distinguish the new cultivar Orange Ice from both its parent and the cultivated *Impatiens sultani* of this type known and used in the floriculture industry:

1. Fully double, orange colored blooms.

2. Even growing, well shaped, mounded plant habit. Reasonably self-branching if propagated from a vegetative cutting.

3. Rooting time is approximately seven days to initiate roots at 70° F.; salable cuttings are available in 21 days at 70° F.

4. Cuttings are produced from either tips or sections. The highest quality cuttings are produced by removing approximately ¼"–½" tip and discarding it. The remaining cutting then branches much better.

5. The foliage is greyed-green, with irregular lighter greyed-green areas along and extending mostly from the midrib. These areas of lighter greyed-green are relatively small in area in proportion to the greyed-green major color. The edges are white with the width and pattern being irregular and varying with maturity and light conditions. Generally, the more sunlight the plant receives the thinner the white margin. At times when newly potted plants are growing extremely rapidly the white margin will become thinner and the green center will have a silver sheen over it.

6. The plant flowers in approximately six weeks from a pinched rooted cutting.

7. When left to reach full bloom, the plant is covered with blossoms which are a deep orange in color.

The new cultivar is similar in many respects to the parent cultivar Rosebud Orange. The primary differences are in the leaf variegation of Orange Ice and its slower, denser growth. The variegation is similar to the variegation of the cultivar Peach Ice, disclosed in U.S. Plant Pat. No. 7,690, but is dissimilar to Peach Ice in most other important characteristics including flower color.

In the accompanying colored photographic drawing.

The photo at the top of the sheet comprises a top perspective view of a typical plant of Orange Ice.

The photo at the bottom of the sheet comprises a closeup view showing several flowers and variegated foliage of the new cultivar, with colors being as true as it is possible to obtain in color reproduction of this type.

The following is a detailed description of my new Impatiens cultivar based on plants produced under commercial practice at Loudon, N.H. Color references are made to The Royal Horticulture Society Colour Chart except where general terms of ordinary dictionary significance are used.

Parentage: Mutation of *Impatiens sultani,* c.v. Orange Ice.

Propagation:

A. *Type cutting.*—Tip or section (section is always near tip).

B. *Time to initiate roots.*—7 days at 21° C. summer, 7 days at 21° C. winter.

C. *Rooting habit.*—Good; roots at nodes or internodes; no hormones needed.

Plant description:

A. *Form.*—Mounded form, with some spreading and slight hanging when given space.

*Habit of growth.*—Slower, denser growth than its green-leaved parent.

C. *Foliage.*—The foliage color is comprised of three colors or shades; relatively darker greyed-green covering a major portion of the leaf, a lighter greyed-green in irregular patterns, and a white margin which varies in width, all in varying percentages. The foliage is generally similar to the foliage of Peach Ice. However, under high light conditions, Orange Ice exhibits much more puckering and leaf twist. 1. Size (mature leaf): Width: 1" to 1¼". Length: 1½" to 2" (excluding petiole). 2. Shape: Ovate, tip acuminate. 3. Texture: Smooth with some wrinkling. 4. Margin: Slightly serrated. 5. Color: The main color of the top side of mature foliage is closest to 191 A, with irregular areas of 191 B-C along and mostly extending from the midvein; margins of leaves are white, in irregular amounts and patterns; on immature foliage, same main colors and white edge, with the white frequently occupying a significant portion of the leaf area, with the main green color becoming more prominent as the leaf matures. However, the final white margin pattern and amount varies significantly from flower to flower. Underside of leaf is slightly lighter with the same white leaf margin. The variegation patterns of Orange Ice including the irregular white margins produce a very attractive appearance. By comparison, the upper surface foliage color of Rosebud Orange is a solid 137 B. 6. Venation: Not distinctive; veins are generally the same color as surrounding tissue, and are alternate.

Flowering description:

A. *Flowering habit.*—Flowers start as a bud the shape of a round ball and the size of a pea, and open similar to a rose in fullness. The flowers open slightly above or even with the foliage.

B. *Flowering.*—Year-round in greenhouse environment, best in spring.

C. *Flowering buds.*—Basically white with a slight touch of light green 145 A; orange color comes out as soon as bud cracks open.

*Quantity of flowers.*—Varies as to maturity; good flower producer.

*Petals.*—Overall inflorescence has an almost rose or camellia type character due to fully double form. 1. Shape: Petals generally round to slightly oblong with indentation in tip. 2. Color: Upper surface: 43 A. Lower surface: 43 C-D. Number of petals: Multiple, up to twenty-five or even more. Size of flowers: 1¼" to 2".

*Reproductive organs.*—1. Stamens: Multiple in number; pollen color yellow. 2. Pistils: Stigma color yellow; styles and ovaries not distinctive.

Disease resistance:

Some resistance to Botrytis. Root fungi are seldom are a problem.

I claim:

1. A new and distinct cultivar of *Impatiens sultani* plant named Orange Ice, as illustrated and described.

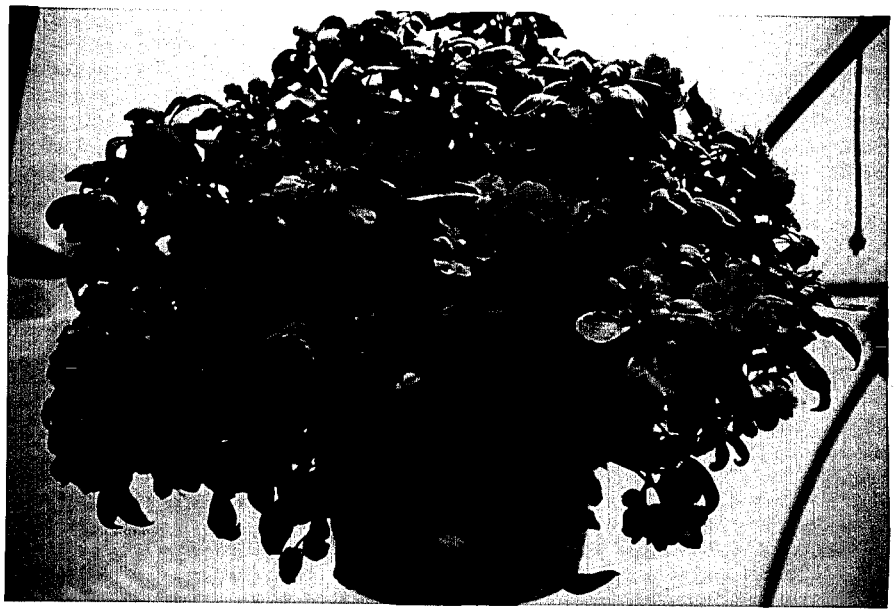
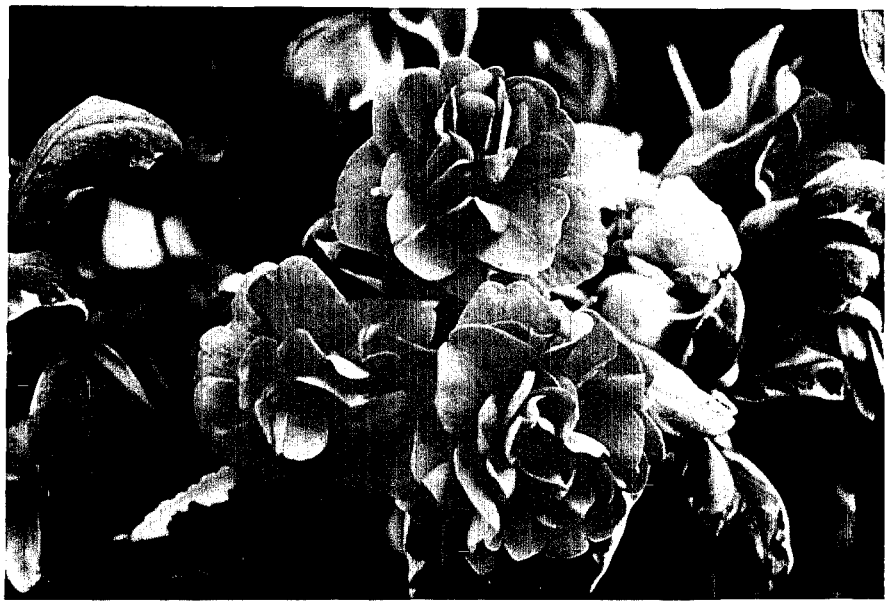

* * * * *